US006815200B1

(12) United States Patent
Krasnykh et al.

(10) Patent No.: US 6,815,200 B1
(45) Date of Patent: Nov. 9, 2004

(54) MODIFIED ADENOVIRUS CONTAINING A FIBER REPLACEMENT PROTEIN

(75) Inventors: Victor N. Krasnykh, Houston, TX (US); David T. Curiel, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/612,852

(22) Filed: Jul. 10, 2000

Related U.S. Application Data

(63) Continuation-in-part of application No. 09/250,580, filed on Feb. 16, 1999, now Pat. No. 6,210,946.
(60) Provisional application No. 60/074,844, filed on Feb. 17, 1998, now abandoned.

(51) Int. Cl.[7] .................... C12N 15/00; C12N 15/09; C12N 15/63; C12N 15/70; C12N 15/74

(52) U.S. Cl. .................... 435/320.1; 435/235.1; 435/455; 435/456; 424/93.2

(58) Field of Search .................... 435/320.1, 455, 435/235.1, 456; 424/93.2; 514/44

(56) References Cited

U.S. PATENT DOCUMENTS

| | | | | |
|---|---|---|---|---|
| 5,770,442 A | 6/1998 | Wickham et al. | ......... | 435/320.1 |
| 5,846,782 A | 12/1998 | Wickham et al. | .......... | 435/69.7 |
| 5,877,011 A | 3/1999 | Armentano et al. | ...... | 435/320.1 |
| 5,885,808 A | 3/1999 | Spooner et al. | .......... | 435/172.3 |
| 6,057,155 A | 5/2000 | Wickham et al. | .......... | 435/325 |
| 6,210,946 B1 * | 4/2001 | Curiel et al. | ............. | 435/235.1 |

OTHER PUBLICATIONS

Wickham et al., Increased in vitro and in vivo gene transfer by adenovirus vectors containing chimeric fiber proteins, 1997,Journal of Virology, pp. 8221–8229.*
Verma et al., Gene therapy–promises, problems and prospects, 1997, NATURE, vol. 389, pp. 239–242.*
Eck et al., Gene–based therapy, 1996, Goodman & Gilman's, The Pharmacological Basis of Therapeutics, pp. 77–101.*
Gall et al., "Adenovirus Type 5 and 7 Capsid Chimera: Fiber Replacement Alters Receptor Tropism Without Affecting Primary Immune Neutralization Epitopes," *J. Virol.*, 70(4): 2116–2123, 1996.
Bergelson, J. et al., "Isolation of a Common Receptor for Coxsackie B Viruses and Adenoviruses 2 and 5," *Science*, 275: 1320–23, 1997.
Tomko, R. et al., "HCAR and MCAR: The human and mouse cellular receptors for subgroup C adenoviruses and group B coxsackieviruses," *Proc. Natl. Acad. Sci.*, 94: 3352–56, 1997.
Krasnykh, V. et al., "Genetic Targeting of Adenoviral Vectors," *Molecular Therapy*, 1: 391–405, 2000.

Wickham, T. et al., "Adenovirus targeted to heparan–containing receptors increases its gene delivery efficiency to multiple cell types," *Nat. Biotechnol.*, 14: 1570–73, 1996.
Dmitriev, I. et al., "An Adenovirus Vector with Genetically Modified Fibers Demonstrates Expanded Tropism via Utilization of a Coxsackievirus and Adenovirus Receptor–Independent Cell Entry Mechanism," *J. Virol.*, 72: 9706–13, 1998.
Vanderkwaak, T. et al., "An Advanced Generation of Adenoviral Vectors Selectively Enhances Gene Transfer for Ovarian Cancer Gene Therapy Approaches," *Gynec. Oncol.*, 74: 227–34, 1999.
Kasono, K. et al., "Selective Gene Delivery to Head and Neck Cancer Cells via an Integrin Targeted Adenoviral Vectors," *Clinical Cancer Research*, 5: 2571–79, 1999.
Hong, J. et al., "Domains Required for Assembly of Adenovirus Type 2 Fiber Trimers," *J. Virol.*, 70: 7071–78, 1996.
Tao, Y. et al., "Structure of bacteriophage T4 fibritin: a segmented coiled coil and the role of the C–terminal domain," *Structure*, 5: 789–98, 1997.
Letarov, A. et al., "The Carboxy–Terminal Domain Initiates Trimerization of Bacteriophage T4 Fibritin," *Biochemistry-(Moscov)*, 64: 817–23, 1999.
Douglas, J. et al., "A system for the propagation of adenoviral vectors with genetically modified receptor specificities," *Nat. Biotechnol.*, 17: 470–75, 1999.
Krasynkh, V. et al., "Characterization of an Adenovirus Vector Containing a Heterologous Peptide Epitope in the HI Loop of the Fiber Knob," *J. Virol.*, 72: 1844–52, 1998.
Von Seggem, D. et al., "Complementation of a fibre mutant adenovirus by packaging cell lines stably expressing the adenovirus type 5 fibre protein," *J. Gen. Virol.*, 79: 1461–68, 1998.
Legrand, V. et al., "Fiberless Recombinant Adenoviruses: Virus Maturation and Infectivity in the Absence of Fiber," *J. Virol.*, 73: 907–19, 1999.

(List continued on next page.)

*Primary Examiner*—Scott D. Priebe
*Assistant Examiner*—Brian Whiteman
(74) *Attorney, Agent, or Firm*—Thomas J. Kowalski; Deborah L. Lu, Ph. D.; Frommer Lawrence & Haug

(57) ABSTRACT

The utility of adenovirus vectors (Ad) for gene therapy is restricted by their inability to selectively transduce disease-affected tissues. This limitation may be overcome by the derivation of vectors capable of interacting with receptors specifically expressed in the target tissue. Previous attempts to alter Ad tropism by genetic modification of the Ad fiber have had limited success due to structural conflicts between the fiber and the targeting ligand. The present invention presents a strategy to derive an Ad vector with enhanced targeting potential by a radical replacement of the fiber protein in the Ad capsid with a chimeric molecule containing a heterologous trimerization motif and a receptor-binding ligand.

16 Claims, 14 Drawing Sheets

OTHER PUBLICATIONS

Davison, E. et al., "The Human HLA–A 0201 Allele, Expressed in Hamster Cells, Is Not a High–Affinity Receptor for Adenovirus Type 5 Fiber," *J. Virol.,* 73: 4513–17, 1999.

Lindner, P. et al., "Specific Detection of His–Tagged Proteins with Recombinant Anti–His Tag scFv–Phosphatase or scFv–Phage Fusions," *BioTechniques,* 22: 140–49, 1997.

Miroshnikov, K. et al., "Engineering trimeric fibrous proteins based on bacteriophage T4 adhesins," *Protein Eng.,* 11: 329–32, 1998.

Efimov, V. et al., "Bacteriophage T4 as a Surface Display Vector," *Virus Genes,* 10: 173–77, 1995.

Gahery–Segard, H. et al., Immune Response to Recombinant Capsid Proteins of Adenovirus in Humans: Antifiber and Anti–Penton Base Antibodies Have a Synergistic Effect on Neutralizing Activity, *J. Virol.,* 72: 2388–97, 1998.

Krasnykh, V. et al., "Generation of Recombinant Adenovirus Vectors with Modified Fibers for Altering Viral Tropism," *J. Virol.,* 70: 6839–46, 1996.

* cited by examiner

FIG. 2 fiber tail
MKRARPSEDTFNPVYPYDTETGPPTVPFLTPPFVSPNGFQESPP

1st repeat of the fiber shaft | 2nd repeat of the fiber shaft | fiber/fibritin junction
GVLSLRLSEPLVTSN | GMALKMGNGLSLDEA | GNLTSQNVYSRLNEI

7th coiled coil of the fibritin
DTKQTTVESDISAIKTSI GYPGNN SIITSVNTNTDNIASINLEL NQSGG

8th coiled coil of the fibritin | 9th coiled coil of the fibritin
IKQRLTVIETSI GSDDIPSS IKGQIKDNTTSIESLNGIV GENTSSG LRA

10th coiled coil of the fibritin | 11th coiled coil of the fibritin
NVSWLNQIV GTDSSGGQPSPPG SLLNRVSTIETSVSGLNNDVQNL

12th coiled coil of the fibritin
QVEI GNNSTG IKGQVVALNTLV NGTNPNGSTVEERG LTNSIKANET

13th coiled coil of the fibritin | trimerization domain of the fibritin
NIASVTQEVNTAKGNISSLQGDVQALQEA GYIPEAPRDGQAYVRK linker | 6His ligand
DGEWVLLSTFLSPA GGGGSGGGGSGGGS RGSHHHHHH (SEQ. ID NO. 13)

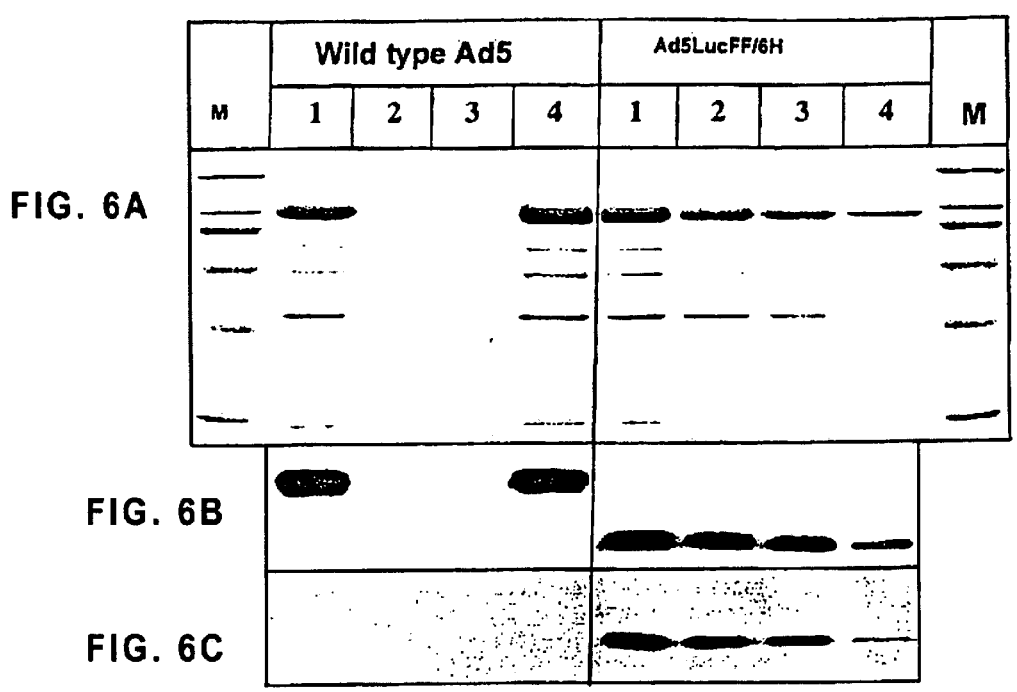

Expected size of PCR product: 1.8Kb

Expected size of PCR product: 1.1Kb

MODIFIED ADENOVIRUS CONTAINING A FIBER REPLACEMENT PROTEIN

CROSS-REFERENCE TO RELATED APPLICATIONS

This continuation-in-part application claims benefit of U.S. application Ser. No. 09/250,580, filed Feb. 16, 1999, now U.S. Pat. No. 6,210,946 issued Apr. 3, 2001, which claims benefit of U.S. provisional application Ser. No. 60/074,844 filed Feb. 17, 1998, now abandoned.

FEDERAL FUNDING LEGEND

This invention was supported in part using federal funds from the National Institutes of Health. Accordingly, the Federal Government has certain rights in this invention.

BACKGROUND OF THE INVENTION

1. Field of the Invention

The present invention relates generally to the fields of vector biology and gene therapy. More specifically, the present invention relates to the production of recombinant adenoviral vectors with replacement of fibers for cell-specific targeting with concomitant elimination of endogenous tropism.

2. Description of the Related Art

Approaches to target adenoviral vectors to specific cell types should be based on an understanding of the mechanism of cell entry exploited by the majority of human adenoviruses and on the identification of the components of the adenoviral virion which are involved in the early steps of the virus-cell interaction. Adenoviruses are non-enveloped viruses containing a double stranded DNA genome packaged into an icosahedral capsid. Whereas the most abundant capsid protein, the hexon, performs structural functions and is not involved in the active cell entry process, the other two major protein components of the capsid, the fiber and the penton base, have been shown to play key roles in the early steps of virus-cell interaction. The fiber and penton base together form penton capsomers consisting of five penton base subunits embedded in the virus capsid tightly associated with a homotrimer of fiber proteins protruding from the virion.

Each of the five subunits of the penton base contains a flexible loop structure, which corresponds to a hypervariable domain of the otherwise highly conserved protein. Amino acid sequence analysis of penton base proteins of different adenoviral serotypes showed that each loop consists of two stretches of alpha helices flanking an arginine-glycine-aspartic acid (RGD) tripeptide positioned in the middle of the loop. Cryo-electron micrography (cryo-EM) studies of Ad2 virions revealed that these loops form 22 Å protrusions on the surface of penton base, thereby facilitating interaction of the RGD motif, localized at the apex of the protrusion with cellular integrins.

The fiber has a well-defined structural organization with each of its three domains, the tail, the shaft, and the knob, performing a number of functions vital for the virus. The short amino terminal tail domain (46 amino acid residues in Ad2 and Ad5 fibers) of the fiber protein is highly conserved among most adenoviral serotypes. In addition to being involved in the association with the penton base protein through an FNPVYD (SEQ ID NO: 15) motif at residues 11–16, which results in anchoring the fiber to the adenoviral capsid, the tail domain also contains near its amino terminus the nuclear localization signal KRλR (where indicates a small amino acid residue), which directs the intracellular trafficking of newly synthesized fibers to the cell nucleus, where the assembly of the adenoviral particle takes place.

The central domain of the fiber is the shaft, which extends the carboxy terminal knob domain away from the virion, thereby providing optimal conditions for receptor binding. The shaft is organized as a sequence of pseudorepeats, each 15 amino acids in length, with a characteristic consensus sequence containing hydrophobic residues at highly conserved positions. This sequence, X-Xφ-X-φ-X-φ-G-X-G-φ-X-φ-X-X or X-X-φ-X-φ-X-φX-X-P-φ-X-φ-X-X, contains hydrophobic amino acids at "φ"-positions, with either the eighth and tenth positions being occupied with two glycines or with a proline in the tenth position. The models for the secondary structure corresponding to these repeats describe the shaft as a triple β-spiral in which the β-strands are oriented more along the fiber axis and the hydrophobic residues at the $7^{th}$ and $13^{th}$ position are located at greater radius. The trimer is stabilized with extensive intra- and inter-chain hydrogen bonding. Due to its rod-like shape, the shaft domain basically determines the length of the entire molecule, which depends on the number of pseudorepeats contained within the shaft. The fibers of various human adenoviral serotypes contain different number of repeats, resulting in a significant variation in the fiber length: from 160 Å (Ad3) to 373 Å (Ad2 and Ad5).

The carboxy terminal knob domain (180–225 amino acid residues) carries out two distinct functions, i.e., initiation of fiber and trimerization and binding of the virus to its primary cellular receptor. X-ray crystallography studies on *E. coli*-expressed Ad5 fiber knob protein have shown that the trimeric knob is arranged around a three-fold crystallographic symmetry axis and resembles a three bladed propeller when viewed along this axis. Each monomer of the knob is a β-sandwich structure, formed by two antiparallel β-sheets R and V. The surface of the V-sheet, which consists of the strands A, B, C, and J, points towards the virion, while the R-sheet, formed by strands D, I, H, and G, points outside the virion and towards the surface of the target cell. These findings have been then corroborated with X-ray crystallography data obtained with recombinant Ad2 fiber knob protein.

A number of studies employing recombinant knobs have shown that these proteins are capable of self-trimerization, which does not require any cellular chaperons. The exact trimerization motif within the fiber knob is largely unknown, which makes mutagenesis or modification of this protein quite difficult: indeed, any new mutation or modification of the fiber may affect amino acid(s) involved in the fiber trimerization and may therefore destabilize the entire molecule, thereby rendering it non-functional. The mutant knobs revealed that deletions in the knob sequence, even as short as two amino acid residues, may result in monomeric fibers, which cannot associate with penton base and, therefore, cannot be incorporated into mature adenoviral particles.

The second function performed by the knob is binding to a cellular receptor and, therefore, mediating the very first step of the virus-cell interaction. This receptor-binding ability of the knob has been demonstrated by utilization of recombinant knob proteins as specific inhibitors of adenoviral binding to cells. Based on the β-sandwich structure of the knob, it was originally hypothesized by Xia et al. that the strands constituting the R-sheet form a receptor binding structure. Recently, however, analysis of fiber knob mutants has revealed that segments outside the R-sheet constitute the receptor-binding site. The Ad5 binding site is located at the side of the knob monomer and specifically involves sequences within the AB and DE loops and B, E, and F β-strands. The binding site of Ad37 that binds to a different receptor involves a critical residue in the CD loop at the apex of the trimer.

The two penton proteins, the penton base and fiber, work in a well-orchestrated manner to provide the early steps of the cell infection mechanism developed by adenoviruses. Importantly, each of these early events is mediated by either fiber or penton base; therefore, both proteins play distinct and well defined roles in this process.

The fiber knob provides the initial high-affinity binding of the virus to its cognate cell surface receptor, coxsackievirus and adenovirus receptor (CAR), which does not possess any internalization functions and merely works as a docking site for Ad attachment.

Human adenoviruses (Ad) of serotype 2 and 5 have been extensively used for a variety of gene therapy applications. This is largely due to the ability of these vectors to efficiently deliver therapeutic genes to a wide range of different cell types. However, the promiscuous tropism of adenovirus resulting from the widespread distribution of coxsackie virus and adenovirus receptor (CAR) (1, 2), limits the utility of adenoviral vectors in those clinical contexts where selective delivery of therapeutic transgene to a diseased tissue is required. Uncontrolled transduction of normal tissues with adenoviral vectors expressing potentially toxic gene products may lead to a series of side effects, thereby undermining the efficacy of the therapy. Furthermore, cell targets expressing CAR below certain threshold levels are not susceptible to adenoviral-based therapies due to their inability to support adenoviral infection. Therefore, the dependence of the efficiency of the adenoviral-mediated cell transduction on the levels of CAR expression by the target cell presents a serious challenge for the further development of adenoviral-based gene therapeutics.

In order to overcome this limitation, the concept of genetic targeting of adenoviral vectors to specific cell surface receptors has been proposed. Strategies to retarget adenoviral vectors are based on the currently accepted model of adenoviral infection (3), which postulates that the initial binding of the adenoviral virion to the cell is mediated by the attachment of the globular knob domain of the adenoviral fiber protein to CAR. This is then followed by an internalization step triggered by the interaction of the RGD-containing loop of a second adenoviral capsid protein, the penton base, with cellular integrins. Although recent studies have shown that representatives of different adenoviral serotypes may utilize cell receptors other than CAR, the two-step mechanism of cell entry established for Ad2 and Ad5 appears to be common to the majority of human adenovirus. As the fiber protein is the key mediator of the cell attachment pathway employed by Ad, genetic incorporation of targeting ligands within this viral protein was originally proposed as the strategy to derive targeted, cell type specific adenoviral vectors.

Although the primary amino acid sequences of fiber proteins of various human and animal adenoviruses are highly diverse, the overall structural and functional organization of these proteins demonstrate remarkable degree of similarity. Indeed, all key features of the domains of the fiber proteins described above—the presence of the nuclear localization signal and the penton base binding site within the fiber tail; the presence of pseudorepeats in the shaft; the propeller-like structure of the knob; and trimeric configuration of the entire fiber molecule—are highly conserved between various adenoviral serotypes. This overall structural and functional similarity has been exploited by a number of investigators, who succeeded in replacing the entire fiber proteins of one adenoviral serotype with those derived from another serotype, or "shuffled" individual domains of the fiber molecule utilizing a variety of structural domains pre-existing in nature.

However, it is of paramount importance to note that fiber shuffling does not overcome the limitations associated with the conserved structure of native fibers: as all the adenoviral fibers characterized so far contain the knob domains of similar structure, which carry out the functions of trimerization and receptor binding, it is logical to assume that replacing those knobs with their structurally similar counterparts derived from other adenoviral serotypes would lead to chimeric molecules inheriting all the drawbacks and structural limitations known for the wild type fibers in the context of incorporation of the cell-targeting ligands within these carrier proteins. The same holds true with respect to shuffling of the full size fibers.

In addition, as all wild type adenoviral fibers have affinity to their cognate receptors, it is rather problematic to create recombinant adenoviral vectors targeted to specific cell surface receptors via the fiber shuffling. This maneuver may change the tropism of the vector, but will never result in an adenoviral vector specifically targeted to the cell of interest. Although ablation of native tropism of adenoviral vector via identification and subsequent elimination of specific amino acids of the fiber protein which mediate binding of the virion to its native receptor is generally viewed as the way of derivation of truly targeted adenoviral vectors, it may have limited utility as the mutated sequences may undergo reversion to the wild type during multiple cycles of virus propagation. Due to its restored ability to bind to its native receptor a virion which genome underwent such a reversion immediately achieves selective advantage over the virions which tropism is restricted to one specific receptor. This selective advantage will eventually result in significant contamination of the vector preparation with virions retaining tropism to receptors different from the target one. Therefore the efficiency of the entire targeting maneuver will b e jeopardized.

Furthermore, many human adenoviruses recognize CAR as the primary binding receptor which is expressed by many different cell types. Taken together with the widespread distribution of adenoviral infections in humans, this has led to the belief that chimeric adenoviral virions incorporating fiber proteins originating from different adenoviral serotypes most likely exist in nature when the same cell in a human body gets infected with two adenoviruses belonging to two different Ad serotypes. Therefore, shuffling the fibers is an experimental realization of the viral chimerizm which takes place naturally.

Attempts to generate adenoviral vectors possessing expanded tropism involved incorporation of short peptide ligands into either the carboxy terminal or so-called HI loop of the knob of the Ad fiber protein. Although these studies demonstrated the feasibility of genetic targeting of Ad and showed the potential utility of such vectors in the context of several disease models (7, 8), further progress in this direction has been hampered by the structural conflicts often observed as a result of modification of the fiber structure. Due to the rather complex structure of the fiber knob domain, even minor modifications to this portion of the molecule may destabilize the fiber, thereby rendering it incapable of trimerization and, hence, non-functional. The upper size limit for a targeting ligand to be incorporated into Ad5 fiber is about 30 amino acid residues (5, 9), which dramatically narrows the repertoire of targeting moieties, thereby limiting the choice of potential ligands and, therefore, cell targets. The task of adenoviral targeting is further complicated by the need to ablate the native receptor-binding sites within the fiber of an adenoviral vector to make it truly targeted. As a result of these limitations, only a handful of heterologous peptide ligands (oligo lysine, FLAG, RGD-4C (SEQ ID NO: 14), RGS(His)$_6$ (SEQ ID NO: 16), and HA epitope) have been successfully used in the context of Ad5 fiber modification during last several years.

The prior art remains deficient in the lack of effective means to produce recombinant adenoviral vectors with combination of novel targeting and ablation of native tropism. The present invention fulfills this longstanding need and desire in the art.

SUMMARY OF THE INVENTION

The present invention describes the next generation of recombinant, cell-specific adenoviral vectors. More particularly, the instant specification discloses that there are two aspects to consider in the modification of adenoviral tropism: (1) ablation of endogenous tropism; and (2) introduction of novel tropism. To expand the utility of recombinant adenoviruses for gene therapy applications, methods to alter native vector tropism to achieve cell-specific transduction are necessary. To achieve such targeting, the present invention discloses the development of a targeted adenovirus created b y radical replacement of the adenovirus fiber protein. The fiber protein was replaced with a heterologous trimerization motif to maintain trimerization of the knobless fiber and a ligand capable of targeting the virion to a novel receptor was introduced simultaneously. The present invention thus represents a demonstration of the retargeting of a recombinant adenoviral vector via a non-adenoviral cellular receptor.

In one embodiment of the present invention, there is provided a recombinant adenovirus vector lacking endogenous viral tropism but having novel tropism. The adenovirus vector is modified to produce a replacement adenoviral fiber protein so as to modify viral tropism, wherein the replaced fiber gene comprises the amino-terminal portion of the adenoviral fiber gene including the tail domain, the carboxy-terminal portion of the T4 bacteriophage fibritin gene and a ligand. The fiber replacing protein retains the fiber's capacity to trimerize. Preferably, the ligand can be a physiological ligand, anti-receptor antibodies or cell-specific peptides. The adenoviral vector may further contains a therapeutic gene such as the herpes simplex virus-thymidine kinase gene.

In another embodiment of the present invention, there is provided a method of killing tumor cells in an individual in need of such treatment, comprising the steps of pretreating said individual with an effective amount of the recombinant adenoviral vector disclosed herein and administering ganciclovir to said individual.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention an d therefore are not to be considered limiting in their scope.

FIG. 2 shows the structure of the fiber-fibritin-6H protein chimera (SEQ ID NO: 13). The FF/6H gene assembled by overlap extension PCR encodes a 373 amino acid long protein chimera which consists of the amino terminal segment of Ad5 fiber protein genetically fused with the carboxy terminal portion of the T4 fibritin protein, followed with the linker and the 6His-containing (SEQ ID NO: 17) ligand. The beginning of the third pseudorepeat of the fiber shaft domain (GNTLSQNV) (SEQ ID NO: 11) is joined to the fibritin sequence starting with the fragment of the insertion loop (SQN) preceding the sixth coiled coil segment of the α-helical central domain of the fibritin (VYSRLNEIDTKQTTVESDISAIKTSI) (SEQ ID NO. 12). The sequence SQNV (SEQ ID NO: 18) present in the native structures of both fusion partners was chosen as the hinge between the two molecules in order to minimize potential structural conflicts between the β-spiral configuration of the fiber shaft and the triple α-helix of the central domain of the fibritin. The segments of the fibritin sequence localized between every two adjacent coiled coils are the insertion loops which provide some degree of flexibility needed for optimal ligand presentation. A peptide linker is incorporated between the carboxy terminal trimerization domain (foldon) of the fibritin and the six histidine containing ligand to extend the ligand away from the carrier protein in order to facilitate binding to the target receptor.

FIG. 5 shows the analysis of Ad5LucFF/6H capsid composition.

FIG. 6 shows the binding of Ad5LucFF/6H virions to Ni-NTA-agarose. Wild type Ad5 or Ad5LucFF/6H were incubated with an aliquot of Ni-NTA-resin for one hour. The matrix was pelleted by centrifugation and the supernatant was removed and then incubated with a second aliquot of Ni-NTA-agarose. Aliquots of material subsequently eluted from the resin, as well as an aliquot of the material present in the supernatant after two sequential incubations with the resin, were separated on a 10% SDS-PAGE gel and then stained (FIG. 6A) or probed with either anti-fiber tail mAb 4D2 (FIG. 6B) or with anti-5His (SEQ ID NO: 19) mAb Penta-His (FIG. 6C). Lane 1, aliquot of the virus prior to incubation with Ni-NTA-agarose; lane 2, material bound to the first aliquot of the resin; lane 3, material bound to the second aliquot of the resin; lane 4, material remaining in the supernatant after two sequential bindings to the resin. Incomplete binding of Ad5LucFF/6H virions to Ni-NTA agarose is most likely due to the small size of pores in the Sepharose CL-6B used as the matrix for manufacturing Ni-NTA-agarose. According to the manufacturer's specifications, the size of those pores does not allow protein molecules with molecular mass larger that 4MDa to enter the pores. Thus, the Ni-NTA groups which are localized on the surface of the Sepharose particles are accessible to the 6His-tagged (SEQ ID NO: 17) virions (relatively small percentage), whereas those hidden inside the pores (the majority) are not.

FIG. 7 shows the analysis of Ad5LucFF/6H genome structure.

FIG. 8 shows the evaluation of the efficiency and receptor-specificity of Ad5LucFF/6H-mediated gene transfer.

DETAILED DESCRIPTION OF THE INVENTION

Figure 1A:
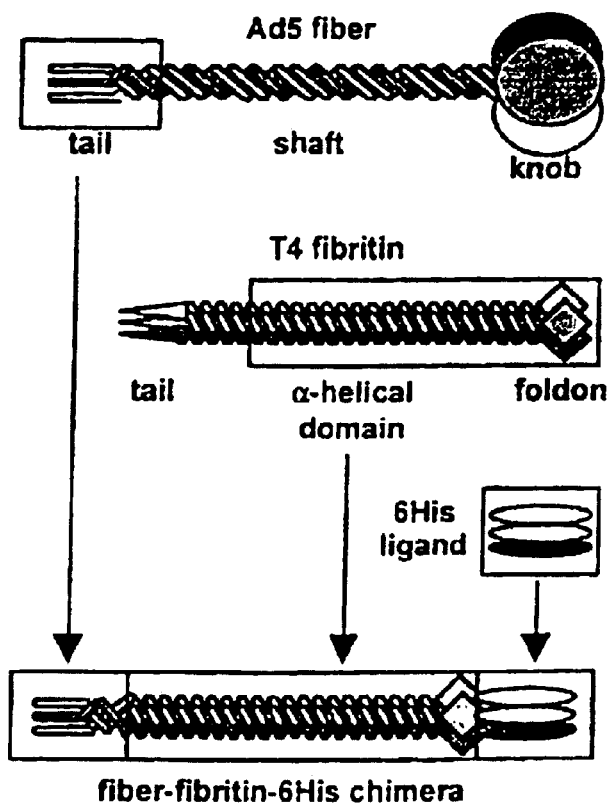
FIG. 1A shows the schema showing key components of the fiber-fibritin-ligand chimera and their sources. The tail of the fiber anchors the fiber-fibritin-6His chimera (SEQ ID NO: 13) in the Ad virion; a fragment of the fibritin protein provides trimerization of the molecule; while the 6His (SEQ ID NO: 17) ligand mediates binding to an artificial receptor.

In marked contrast to the strategy of replacing one Ad fiber (or one of its domains) with the fiber (or its domain) derived from a different Ad serotype, the present invention presents a n alternative approach of Ad targeting based on replacement of the native fiber in an Ad capsid with a chimeric protein, rationally designed to result in permanent ablation of native Ad receptor tropism and simultaneously offers unprecedented flexibility in the generation of novel vector tropism. This work was driven by the hypothesis that these goals may be achieved by "splitting" the functions normally performed by the knob domain of the Ad5 fiber between two different protein moieties which would replace the knob. Specifically, the knob of the fiber was replaced with a heterologous trimerization motif to maintain trimerization of the knobless fiber and a ligand capable of targeting the virion to a novel receptor was introduced simultaneously. Therefore, in marked contrast to the previous, mostly unsuccessful, attempts to fit a desired ligand into the highly complex framework of the fiber knob domain, the present invention employs a radical replacement of the fiber with a protein chimera, which allows for utilization of a virtually unlimited range of targeting protein ligands in the context of Ad vector system.

The present invention is directed to vector system that provides both a highly efficient and specific targeting of adenovirus vector for the purpose of in vivo gene delivery to predefined cell types after administration. In the recombinant adenovirus of the present invention, the adenovirus is modified by replacing the adenovirus fiber protein with a fiber replacement protein. In a preferred embodiment, the fiber replacement protein comprises: a) an, amino-terminal portion comprising an adenoviral fiber tail domain; b) a chimeric fiber replacement protein; and c) a carboxy-terminal portion comprising a targeting ligand. A person having ordinary skill in this art would recognize that one may exploit a wide variety of genes encoding e.g. receptor ligands or antibody fragments which specifically recognize cell surface proteins unique to a particular cell type to be targeted.

The following description will allow a person having ordinary skill in this art to determine whether a putative fiber replacement protein would function as is desired in the compositions and methods of the present invention. Generally, the fiber replacement protein associates with the penton base of the adenovirus. To prevent problems of incompatibility, the amino-terminus of the chimeric protein can be genetically fused with the tail domain of the adenovirus fiber. Structurally, the fiber replacement protein is preferably a rod-like, trimeric protein. It is desirable for the diameter of the rod-like, trimeric protein to b e comparable to the native fiber protein of wild type adenovirus. It is important that the fiber replacement protein retain trimerism when a sequence encoding a targeting ligand is incorporated into the carboxy-terminus. In a preferred aspect, a representative example of a fiber replacement protein is T4 bacteriophage fibritin protein. More generally, the fiber replacement protein can be any native or chimeric protein which is capable of associating with the Ad5 penton base protein and bind to specific cell surface receptor. Other Representative examples of fiber replacement proteins include isoleucine trimerization motif and neck region peptide from human lung surfactant D. Preferably, the fiber replacement protein has a coiled coil secondary structure. The secondary structure provides stability because of multiple interchain interactions.

In one embodiment, the fiber-replacing molecule engineered in this study incorporated the tail and two amino terminal repeats of the shaft domain of the Ad5 fiber protein genetically fused with a truncated form of the bacteriophage T4 fibritin protein, which was employed as the heterologous trimerizing motif in order to compensate for the knob deletion (FIG. 1A). The choice of the T4 fibritin as the trimerization moiety was dictated by a number of its structural features. The fibritin protein is a product of the wac gene which forms the "collar" and the "whiskers" of the T4 capsid, where it mediates assembly of the long tail fibers and their subsequent attachment to the tail baseplate. Trimerization of this rod-like, 486 amino acid long protein is initiated and maintained by the short (30 aa long) carboxy terminal domain or "foldon", which is stabilized by a number of hydrophobic interactions and hydrogen bonds (10). The central α-helical domain of fibritin, which consists of 13 segments of parallel triple coiled-coils separated by flexible loop structures, passively follows the trimerization initiated at the carboxy terminal of the molecule. The trimeric structure of fibritin is extremely stable and is not compromised by either extensive amino terminal deletions (up to 92% of the molecule) (11) or carboxy terminal insertions up to, at least, 163 aa long (11, 12). For the purposes of this study, no receptor-binding function has been shown for fibritin.

Figure 3:
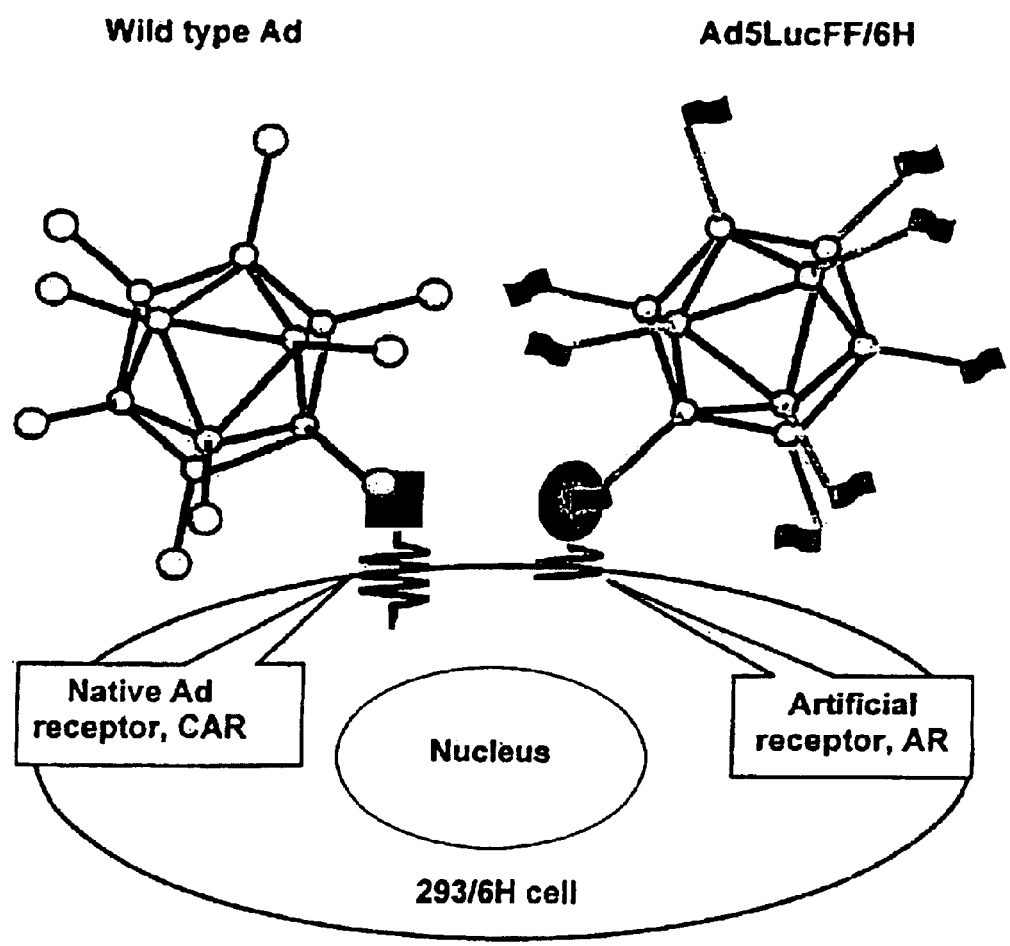
FIG. 3 shows the Ad-mediated gene transfer to 293/6H cells. 293/6H cells were derived by transfection of 293 cells with a recombinant plasmid expressing an artificial receptor (AR), which consists of an anti-5His (SEQ ID NO: 19) scFv genetically fused with the transmembrane domain of the PDGF receptor. Due to the presence of both CAR and AR on the surface of these cells, 293/6H are susceptible to infection by both the Ad with the wild type fibers and the Ad incorporating the FF/6H chimera. Importantly, each virus is capable of binding to only one type of receptor, CAR or AR. The progenitor cell line, 293, is refractory to Ad5LucFF/6H infection.

In order to provide a receptor-binding ligand, a carboxy terminal six-histidine sequence was connected to the fibritin protein of this fiber-fibritin chimera via a short peptide linker (FIG. 2). The purpose of this maneuver was to demonstrate the feasibility of targeting of fibritin-containing Ad vectors to alternative cell-surface receptors by directing the modified vector to an artificial receptor, which is expressed on the surface of 293/6H cells (FIG. 3). The extracellular domain of this artificial receptor (AR) is an anti-5His (SEQ ID NO: 19) single chain antibody, which is genetically fused with the transmembrane domain of the platelet derived growth factor receptor (13). In addition to receptor binding, this 6His (SEQ ID NO: 17) sequence was employed to facilitate the detection and purification of the FF/6H chimeras and Ad virions incorporating this protein.

In the adenovirus of the present invention, the targeting ligand is selected from the group consisting of physiological ligands, anti-receptor antibodies, cell-specific peptides and single chain antibodies. In one embodiment, the adenovirus carries in its genome a therapeutic gene. A representative example of a therapeutic gene is a herpes simplex virus thymidine kinase gene.

The present invention is also directed to a method of killing tumor cells in an individual in need of such treatment, comprising the steps of: pretreating said individual with an effective amount of the adenovirus of the present invention; and administering ganciclovir to said individual.

In accordance with the present invention, there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

As used herein, "chimera" or "chimeric" refers to a single polypeptide possessing multiple components, often but not necessarily from different organisms. As used herein, "chimeric" is used to refer to tandemly arranged protein moieties that have been genetically engineered to result in a fusion protein possessing regionS corresponding to the functions or activities of the individual protein moieties.

As used herein, the terms "fiber gene" refer to the gene encoding the adenovirus fiber protein. As used herein, "chimeric fiber protein" refers to a modified fiber as defined above.

A "fiber replacement protein" is a protein that substitutes for fiber and provide three essential features: trimerizes like fiber, lacks adenoviral tropism and has novel tropism.

As used herein the term "physiologic ligand" refers to a ligand for a cell surface receptor.

In addition, the invention may includes portions or fragments of the fiber or fibritin proteins. As used herein, "fragment" or "portion" as applied to a protein or a polypeptide, will ordinarily be at least 10 residues, more typically at least 20 residues, and preferably at least 30 (e.g., 50) residues in length, but less than the entire, intact sequence. Fragments of these genes can be generated by methods known to those skilled in the art, e.g., by restriction digestion of naturally occurring or recombinant fiber or fibritin genes, by recombinant DNA techniques using a vector that encodes a defined fragment of the fiber or fibritin gene, or b y chemical synthesis.

The following examples are given for the purpose of illustrating various embodiments of the invention and are not meant to limit the present invention in any fashion.

EXAMPLE 1

Construction of the Fiber-Fibritin-6His (SEQ ID NO: 13) (F/61H) chimera Generation of the gene encoding the fiber-fibritin-6His chimera was done in several steps. First, a segment of the fibritin gene was PCR-amplified and used to substitute most of the fiber gene sequence encoding the shaft domain. For this, a portion of the T4 fibritin gene encoding the sixth coiled coil through the C-terminal of the protein was amplified with a pair of primers "FF.F" (GGG AAC TTG ACC TCA CAG AAC GTT TAT AGT CGT TTA AAT G) (SEQ ID NO. 1) and "FF.R" (AGG CCA TGG CCA ATT TTT GCC GGC GAT AAA AAG GTA G) (SEQ ID NO. 2). The product of this PCR encodes a segment of an open reading frame (ORF) containing four amino terminal (GLNT) (SEQ ID NO: 20) and three carboxy terminal (KIG) codons of the fiber shaft sequence fused to the fibritin sequence. The reverse primer introduces a silent mutation at the 3' end of the fibritin open reading frame resulting in generation of a unique NaeI-site. Also, NcoI-site was incorporated in the "FF.F" in order to fuse the open reading frame of the fiber and the fibritin. The product of the PCR was then cleaved with NcoI and cloned in the fiber shuttle vector pNEB.PK3.6 (22) cut with NaeI and NcoI. As a result of this cloning, an original NaeI-site in the fiber open reading frame was destroyed, therefore NaeI-site at the end of the fibritin open reading frame remains unique. The plasmid generated was named pNEB.PK.FFBB. This fusion procedure resulted in an open reading frame, in which the fiber and the fibritin sequence were joined via an SQNV peptide (SEQ ID NO: 18) hinge, present at the beginning of the 3rd repeat of Ad fiber shaft as well as at the 6' coil coiled segment of the fibritin.

At the next step, a portion of 3' terminal sequence of $FF_{BB}$ open reading frame was replaced with synthetic oligo duplex in order to introduce in the construct a unique restriction site, SwaI, which would allow modifications of the 3' end of the gene. To reach this end, a duplex made of oligos "F5. Δ3Swa.T" (TTG GCC CCA TTT AAA TGA ATC GTT TGT GTT ATG TTT CAA CGT GTT TAT TTT TC) (SEQ ID NO. 3) and "F5. Δ3.Swa.B" (AAT TGA AAA ATA AAC ACG TTG AAA CAT AAC ACA AAC GAT TCA TTT AAA TGG GGC CAA TAT T) (SEQ ID NO. 4) was cloned in BstXI-MfeI-digested pNEB.PK3.6, thereby generating pNEB.PKΔ3.

To facilitate the downstream manipulation with the 3' end of the fiber-fibritin gene a plasmid pNEB.PK.$FF_{BB}$Δ3 was generated as follows: an NcoI-Acc65.I-fragment in pNEB-.PK$FF_{BB}$ was replaced with an NcoI-Acc65.I-fragment from pNEB.PKΔ3.

The plasmid pXK.$FF_{BB}$Δ3 was obtained from pNEB.P-K.$FF_{BB}$Δ3 by deleting a XbaI-fragment containing a portion of the Ad5 Luc-3 DNA. This was done in order to eliminate a BamHI-site contained in this XbaI fragment, which would otherwise compromise the utility of the BamHI-site introduced into the construct at a later step (see below).

To add the sequence encoding a C-terminal linker to the fiber/fibritin fusion protein, a synthetic oligo duplex consisting of oligos "$FF_{BB}$LL.T" (GGC AGG TGG AGG CCG TTC AGG CGG AGG TGG CTC TGG CGG TGG CGG ATC CGG GGA TTT) (SEQ ID NO. 5) and "$FF_{BB}$LL.B" (AAA TCC CCG GAT CCG CCA CCG CCA GAG CCA CCT CCG CCT GAA CCG CCT CCA CCT GCC) (SEQ ID NO. 6) was cloned into NaeI-SwaI-digested pXK.$FF_{BB}$Δ3, generating PXK.$FF_{BB}$LL. The duplex contains a BamHI-site at the 3'-end of the linker-encoding sequence. Of note, this cloning procedure left both the NaeI- and the SwaI-sites intact and, therefore available for subsequent cloning steps.

An RGS (His)$_6$-encoding sequence (SEQ ID NO: 16) was fused to the 3' end of the $FF_{BB}$LL gene by inserting a synthetic oligo duplex made of oligos "RGS6H.T" (GAT CTA GAG GAT CGC ATC ACC ATC ACC ATC ACT AAT) (SEQ ID NO. 7) and "RGS6H.B" (ATT AGT GAT GGT GAT GGT GAT GCG ATC CTC TA) (SEQ ID NO. 8) into BamHI-SwaI-digested pXK.$FF_{BB}$LL. The resultant plasmid was designated pXK.FF/6H. This cloning procedure destroyed both the BamHI- and the SwaI-sites. This completed the derivation of the shuttle plasmid containing the FF/6H gene.

In order to express the FF/6H protein in E. coli, the FF/6H assembled in pXK.FF/6H was PCR amplified using the primers "FF.F(BspHI)" (CCC TCA TGA AGC GCG CAA GAC CGT CTG) (SEQ ID NO. 9) and (CCC AAG CTT AGT GAT GGT GAT GGT GAT) (SEQ ID NO. 10), digested with NcoI and HindIII and cloned into NcoI-HindIII-cut pQE60 resulting in pQE.FF/6H.

In order to derive recombinant adenoviral genome containing FF/6H gene, an EcoRI-XbaI-fragment of pXK.FF/6H was used for recombination with SwaI-digested pVK500 (6), resulting in pVK511. The luciferase expressing cassette was then incorporated in place of the E1 region of the adenoviral genome contained in pVK511 via homologous DNA recombination between ClaI-digested pVK511 and a fragment of pACCMV.LucΔPC. The plasmid generated was designated pVK7ll. The virus of interest, Ad5LucFF/6H, was then rescued by transfecting 211B cells (15) with PacI-digested pVK711.

EXAMPLE 2

Characterization of Recombinant Adenovirus Expressing the Fiberfibritin-6His (SEQ ID NO: 13)(FF/6H) Chimera.

Figure 1B:
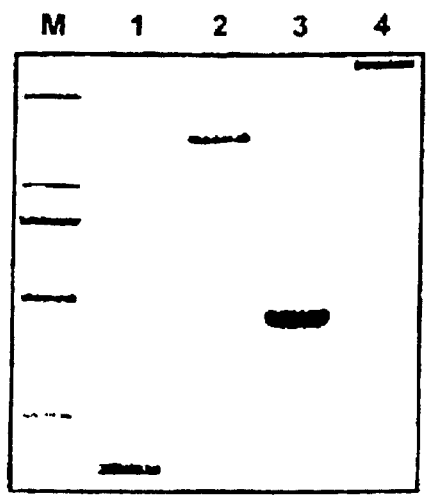
FIG. 1 shows the generation of Ad5 fiber-T4 fibritin chimera containing targeting ligand.

For the purposes of preliminary characterization, the FF/6H chimeric protein was initially expressed in E. coli and purified on a Ni-NTA-agarose column. Subsequent SDS-PAGE analysis of the purified chimeric protein proved that it is trimeric and that the FF6H trimers are as stable in an SDS-containing gel as the trimers of the wild type Ad5 fiber (FIG. 1B). Efficient binding of the FF/6H protein to a Ni-NTA-containing matrix proved that the 6His ligand (SEQ ID NO: 17) was available for binding in the context of this trimeric molecule. According to this analysis, truncated T4 fibritin incorporated into the FF/6H protein was able to direct trimerization of the chimera and also successfully served the purposes of ligand presentation, thereby satisfying two key functional criteria of an ideal fiber-replacing molecule.

Figure 4:
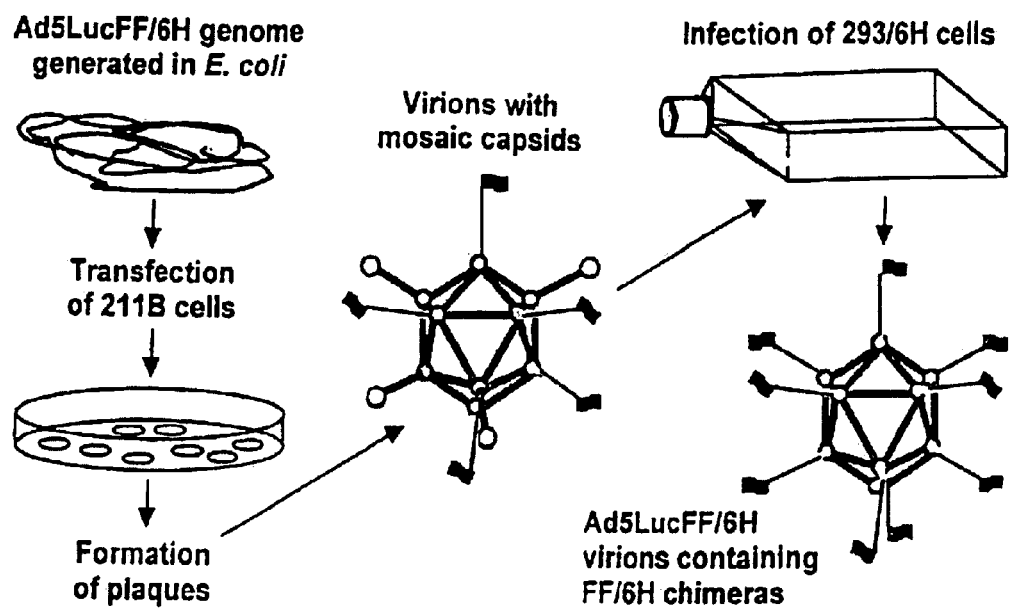
FIG. 4 shows the generation of Ad5LucFF/6H. The genome of the wild type Ad5 was modified by homologous DNA recombination in E. coli to contain a firefly luciferase expressing cassette in place of the E1 region, as well as the gene encoding the FF/6H chimera, which replaced the wild type fiber gene. The virus, Ad5LucFF/6H, was first rescued in 211B cells expressing the wild type Ad5 fiber. The seed stock of the virus obtained at this point contained a mixed population of Ad virions with mosaic capsids incorporating both wild type Ad5 fibers and FF/6H proteins. In order to obtain a homogeneous population of Ad virions containing FF/6H chimeras, this stock was then used to infect 293 cells expressing the artificial receptor, 293/6H. The virus isolated from 293/6H cells was purified by double banding on a CsCl gradient.

In order to evaluate the functional utility of the FF/6H chimeras incorporated into a mature adenoviral particle, homologous recombination in *E. coli* (14) was employed to insert the FF/6H encoding gene into the genome of E1-deleted, firefly luciferase-expressing Ad5 in place of the wild type fiber gene. The virus of interest, Ad5LucFF/6H, was then rescued by transfection of 211B cells with the resultant adenoviral genome (FIG. 4). 211B cells, a derivative of 293 cells which constitutively express the wild type Ad5 fiber protein (15), were chosen for this transfection experiment in order to guarantee the success of the virus rescue. Ad5LucFF/6H was further expanded on 211B cells and purified by double banding in a CsCl gradient. At this point, the viral stock contained mosaic virions bearing a mixture of the wild type fibers and FF/6H chimeras (data not shown). In order to obtain a homogenous population of Ad5LucFF/6H virions lacking the wild type fibers, but exclusively incorporating FF/6H proteins, the original viral stock was then used to infect 293/6H cells at multiplicity of infection of 1000 viral particles per cell. CsCl gradient purification of Ad5LucFF/6H virions isolated from the lysates of infected 293/6H cells 72 hours post infection (at which point a complete cytopathic effect was observed) resulted in a yield of $3 \times 10^4$ viral particles per cell, which was well within the range of yields characteristic for E1-deleted Ad5 vectors.

Figure 5A:
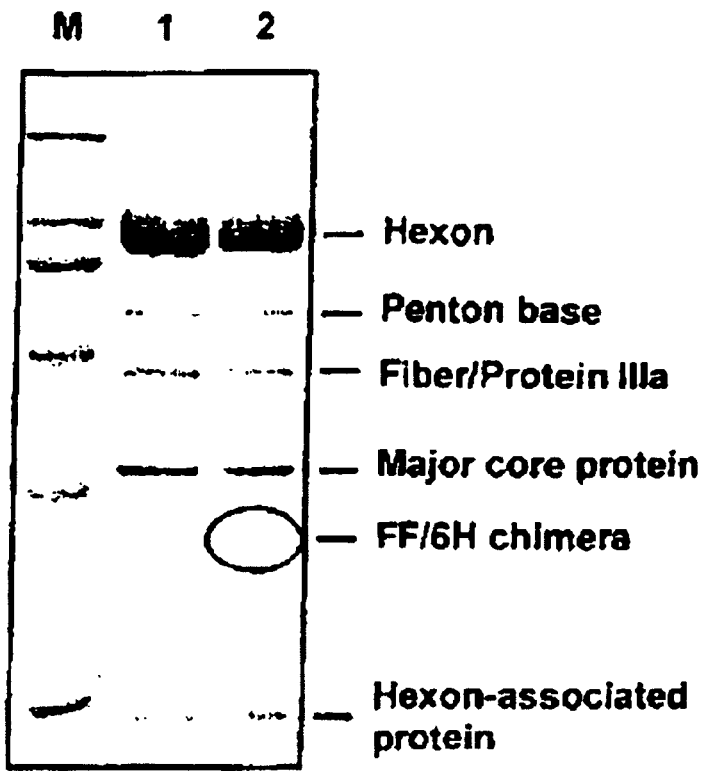
FIG. 5A shows SDS-PAGE of CsCl-purified Ad5LucFF/6H virions. Samples containing 4×10$^{10}$ particles of either the wild type Ad5 (lane 1) or Ad5LucFF/6H (lane 2) were boiled in Laemmli sample buffer and fractionated on a 10% SDS-PAGE gel. Of note, the resolution of this minigel is not sufficient for separation of the fiber and protein IIIa.
Figure 5B:
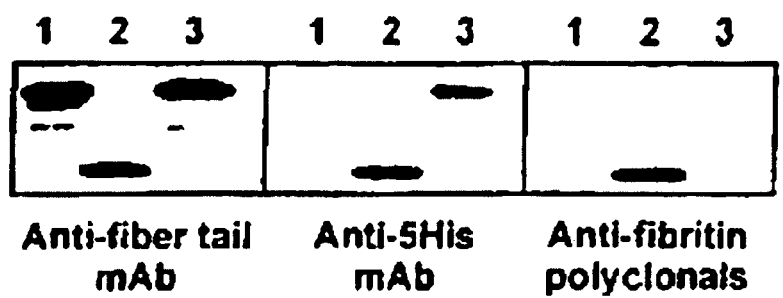
FIG. 5B shows Western blot analysis of FF/6H chimeras incorporated into Ad5LucFF/6H virions. Proteins of denatured Ad5LucFF/6H virions, lane 2, were separated on a 10% SDS-PAGE gel and then probed with anti-Ad fiber tail mAb 4D2, anti 5His (SEQ ID NO: 19) mAb Penta-His and anti-fibritin mouse polyclonal antibodies. Wild type Ad5, lane 1, and Ad5LucFc6H, a virus containing fibers with carboxy terminal 6His tags (SEQ ID NO: 17), lane 3, were used as controls.

The next goal was to demonstrate that the FF/6H chimeras had been incorporated into the Ad5LucFF/6H capsids. Since fiberless Ad5 virions have been successfully purified on CsCl gradients by others (15, 16), it was possible that the putative Ad5LucFF/6H virions isolated in our study could have lacked FF/6H proteins. This was ruled out by SDS-PAGE of purified Ad5LucFF/6H virions and a Western blot analysis utilizing anti-sera specific to all three major components of FF/6H chimera, the fiber tail, the fibritin and the 6His ligand (SEQ ID NO: 17) (FIGS. 5A and B). These assays showed that the capsid of Ad5LucFF/6H virions consists of completely matured Ad proteins and incorporates full-size FF16H chimeras. As expected, no wild type fibers were found in this preparation of Ad5LucFF/6H. These findings were further corroborated in an experiment involving binding of purified Ad5LucFF/6H virions to Ni-NTA-resin: in contrast to the Ad vector containing wild type fibers, which did not bind to the matrix, Ad5LucFF/6H demonstrated 6His-mediated (SEQ ID NO: 17) binding to the resin (FIG. 6). Therefore, in addition to its ability to assume a trimeric configuration and bind to a receptor-mimicking molecule, the FF/6H chimera also retained the capacity of being incorporated into mature Ad capsids.

Figure 7A:
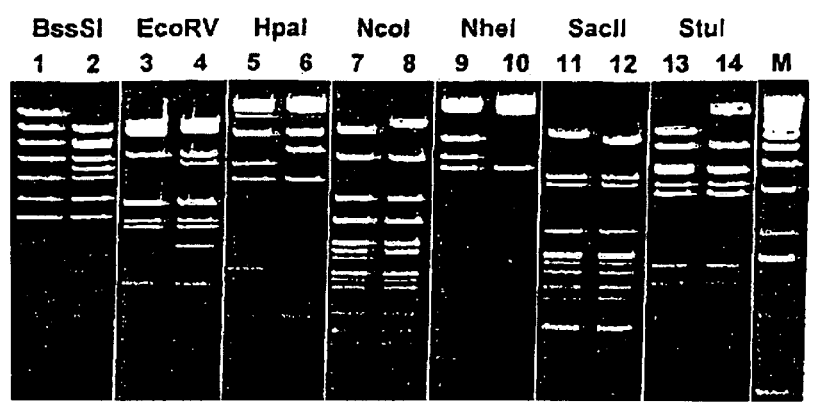
FIG. 7A shows DNA isolated from purified Ad5LucFF/6H virions subjected to restriction enzyme analysis using a number of restriction endonucleases which do not cleave the wild type fiber gene sequence but cleave the FF/6H gene. Odd-numbered lanes—control Ad5Luc1 DNA; even-numbered lanes—Ad5LucFF/6H DNA.
Figure 7B:
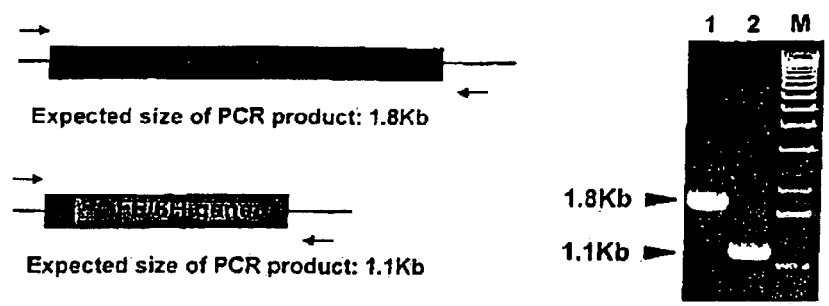
FIG. 7B shows "diagnostic PCR" utilizing a pair of primers flanking the fiber gene in Ad5 genome employed to show the absence of the wild type fiber gene sequence in the Ad5LucFF/6H genome: lane 1, PCR product amplified from wild type Ad5 DNA; lane 2, PCR product amplified from Ad5LucFF/6H DNA; M—1 Kb ladder.

Restriction enzyme analysis of the Ad5LucFF/6H genome, diagnostic PCR utilizing a pair of primers flanking the fiber gene in Ad5 genome and partial sequencing of Ad5LucFF/6H DNA demonstrated that the viral genome was stable and that the only fiber-encoding gene present was the FF/6H gene (FIG. 7). This set of experiments completed the molecular characterization of Ad5LucFF/6H by confirming both the identity and the integrity of the virus capsid and its genome.

Figure 8A:
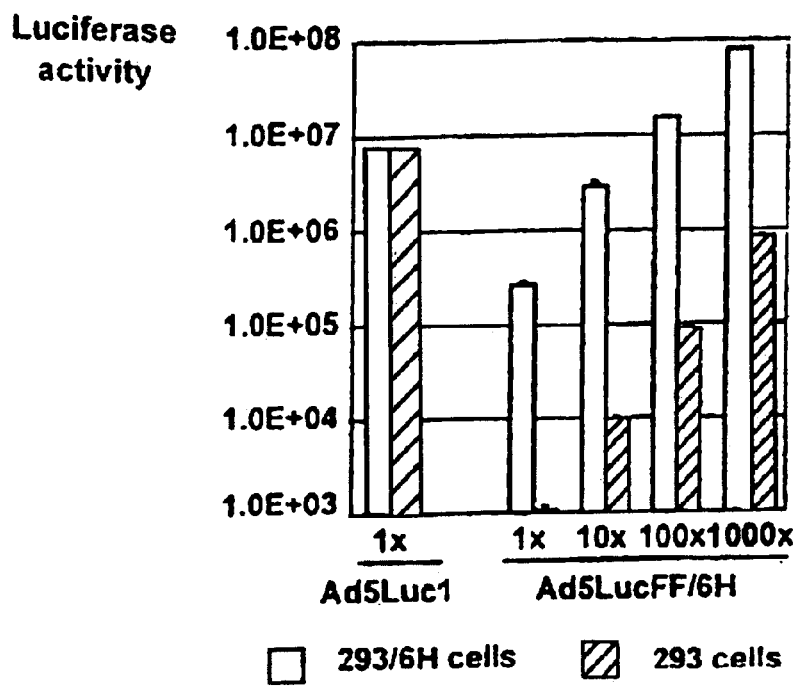
FIG. 8A shows gene transfer to 293 and 293/6H cells. Cells seeded in 24-well plates were infected with various doses of Ad5LucFF/6H. The minimal viral dose corresponding to a multiplicity of infection of 40 viral particles per cell, (1×), was equal to the dose of the control virus, Ad5Luc1, whereas Ad5LucFF/6H doses 10×, 100×, and 1000×contained 10-, 100-, and 1000-times the amount of the control virus, correspondingly. Twenty hours post-infection, the cells were collected, lysed, and the luciferase activity of the lysates was measured in relative light units.

The ability of Ad5LucFF/6H to deliver a transgene to the target cells was then evaluated in a series of studies employing this viral vector for infection of 293/6H cells expressing an artificial receptor capable of binding proteins and Ad virions possessing a 6His tag (SEQ ID NO: 17) (FIG. 3). First, the gene transfer capacity of Ad5LucFF/6H was compared to that of an isogenic Ad vector, Ad5Luc1, bearing wild type fibers (FIG. 8A). The doses of both viruses used in this experiment were normalized based on the particle titers of the viral preparations, which also correlated well with the total protein concentration of the samples. Due to the significant differences in the dissociation constants ($k_d$) previously determined for the Ad5 fiber/CAR interaction (17), $4 \times 10^{-9}$ M, and for the 5 His/anti-5His (SEQ ID NO: 19) mAb 3D5 interaction (18), $4.75 \times 10^{-7}$ M, lower efficiency of the gene transfer for Ad5LucFF/6H vector was expected.

In order to compensate for potentially lower infection levels resulting from this difference in binding affinities, several different doses of Ad5LucFF/6H vector WERE was useD, of which the lowest corresponded to the dose of the control vector. This experiment showed that Ad5LucFF/6H was capable of efficient transgene delivery to the target cells. However, at equal multiplicities of infection the level of transgene expression in Ad5Luc1-infected cells (293 and 293/6H) was 30-fold higher than that registered in 293/6H cells infected with Ad5LucFF/6H. Importantly, there was an two orders of magnitude increase in Ad5LucFF/6H-expressed luciferase activities detected in 293/6H cells expressing AR compared to parental 293 cells infected with the same vector. This differential in the transgene expression levels strongly suggests that Ad5LucFF/6H-mediated gene transfer to 293/6H occurred in a CAR-independent, receptor-specific manner via interaction of the virus with the AR.

Figure 8B:
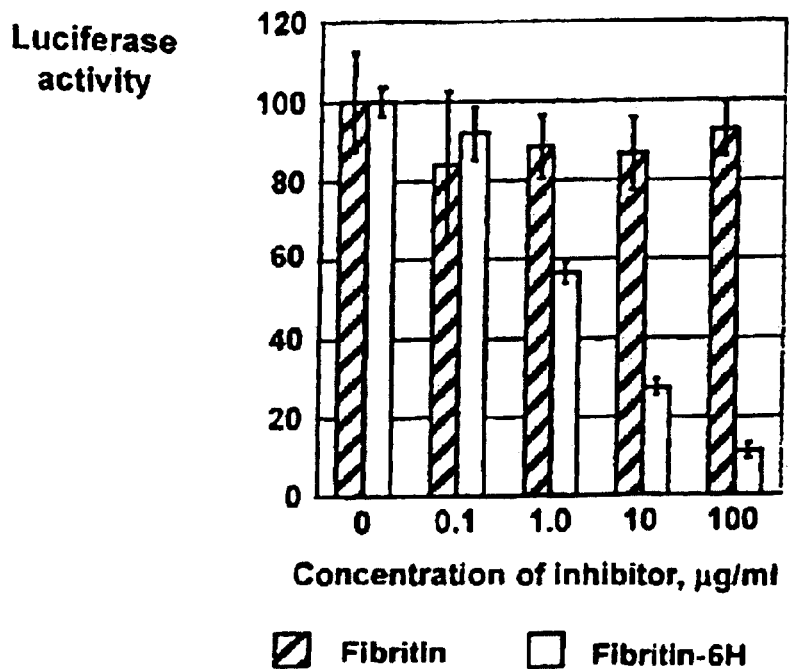
FIG. 8B shows the specificity of Ad5LucFF/6H binding to the artificial receptor. 293/6H cells grown in monolayer culture were pre-incubated with various concentrations of either the truncated form of fibritin or fibritin carrying a carboxy terminal 6His tag (SEQ ID NO: 17) fibritin-6H, prior to infection with Ad5LucFF/6H. Luciferase activities detected in the lysates of infected cells twenty hours postinfection were given as percentages of the activity in the absence of blocking protein. Each data point was set in triplicates and calculated as the mean of three determinations.

The next gene transfer experiment employed two different forms of recombinant fibritin proteins as blocking agents, of which only one, fibritin-6H, contained a carboxy terminal 6His tag (SEQ ID NO: 17) (FIG. 8B). The purpose of this assay was to provide additional evidence that the backbone of the fibritin molecule does not contribute to binding to AR or any other cell surface receptor. Dose-dependent inhibition of Ad5LucFF/6H infection of 293/6H cells with fibritin-6H, but not with the fibritin lacking the 6His tag (SEQ ID NO: 17), further proved that this tag is the component of the virion solely responsible for the binding of the virus to the AR.

The present invention has developed a novel approach to the modification of adenoviral vector tropism by replacing the receptor-binding fiber protein in the adenoviral capsid with an artificial protein chimera. The rational design of this chimera, based on the general structural similarity of the Ad5 fiber and bacteriophage T4 fibritin, has resulted in the derivation of a novel ligand-presenting molecule. The most important difference from the wild type fiber protein is the disengagement of the trimerization and the receptor-binding functions normally performed by the fiber knob domain. As a result of this distribution of functions, the receptor specificity of the re-engineered Ad5 vector may now be defined by a domain of the chimera which plays no role in the trimerization of the molecule, and may therefore be manipulated without the risk of destabilizing the ligand-presenting protein and the virion. The use of T4 fibritin for ligand display suggests that a wide variety of heterologous targeting ligands, including large polypeptide molecules, may be employed in the context of the fiber-fibritin chimera described here.

Fibritin chimeras analogous to the one described in this work may be viewed as versatile ligand-displaying molecules suitable for genetic modification of virtually any human or animal adenoviral vector. The problem of elimination of undesirable natural tropism of native fibers contained in the adenoviral virion may thus be solved by substitution of native fibers with such fibritin chimeras. This approach has significant advantage over maneuvers involving the identification and subsequent mutagenesis of the native receptor binding sites within the fibers of numerous adenoviral species, some of which are able to bind to different types of primary receptors. In addition, this strategy eliminates the risk of reversion of the mutated fiber gene to the wild type during multiple rounds of propagation, which would compromise the efficiency of any vector targeting schema.

An additional advantage offered by adenoviral vectors incorporating the fibritin-based chimeras for the purposes of human gene therapy because of interference of anti-fiber antibodies present in the serum of some gene therapy patients with the adenoviral vectors used in clinical protocols. Importantly, these antibodies have been shown to have a synergistic effect on adenoviral vector neutralization when present together with anti-penton base antibodies. Thus, deletion of the most of the fiber sequence in the fibritin-bearing adenoviral vectors would make them refractory to this type of immune response and therefore more efficient as therapeutic agents.

EXAMPLE 3

Figure 9:
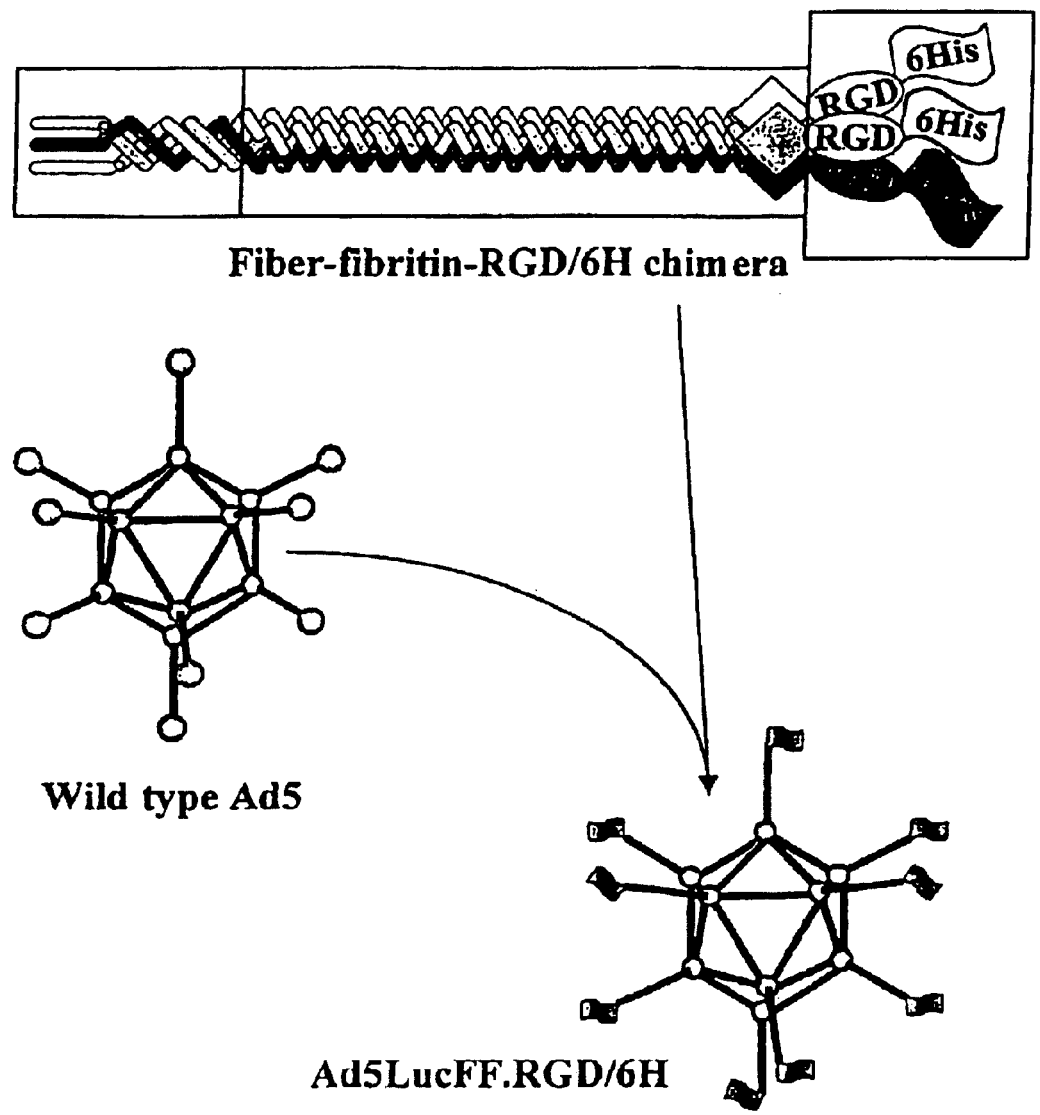
FIG. 9 shows the schema of key components of the fiber-fibritin-RGD/6His chimera (SEQ ID NO:16).

Characterization of Recombinant Adenovirus Expressing the Fiberfibritin-RGD-6His (SEQ ID NO: 13) (FF.RGD/6H) Chimera A second adenoviral vector, Ad5luc.FF.RGD/6H, containing fiber-fibritin chimeras incorporating at their carboxy termini two peptide ligands RGD-4C (CDCRGDCFC) (SEQ ID NO. 14) and 6His (SEQ ID NO: 17) was generated (FIG. 9). The virus was propagated in 293 cells and purified on CsCl gradient according to standard technique.

Figure 10:
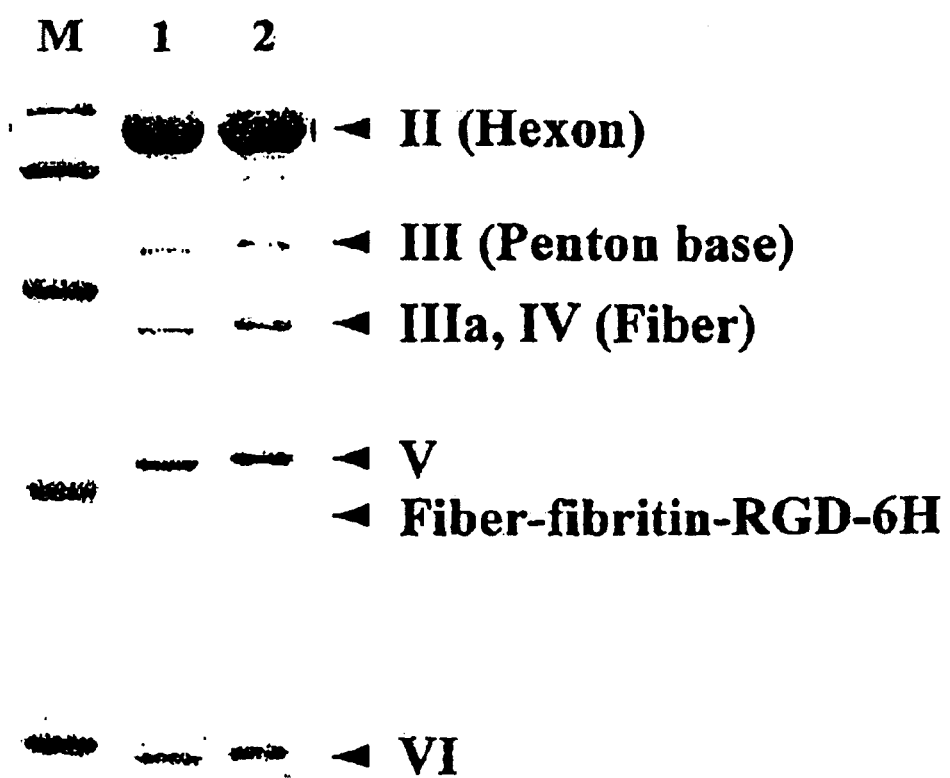
FIG. 10 shows SDS-PAGE analysis of CsCl-purified Ad5LucFF.RGD/6H virions. Samples of either the wild type Ad5 (lane 2) or Ad5LucFF.RGD/6H (lane 1) were boiled in Laemmli sample buffer and fractionated on a 10% SDS-PAGE gel.

The protein composition of Ad5luc.FF.RGD/6H was verified by SDS-PAGE using the virus with wild type capsids as a control. As shown in FIG. 10, all major protein components of Ad5luc.FF.RGD/6H are essentially the same as those of control adenoviral capsid. The only difference noted between the capsid protein patters demonstrated by the two viruses was the presence of the FF.RGD/6H chimeras in the Ad5LucFF.RGD/6H particles in place of the wild type fibers contained in the capsids of the control adenovirus.

Figure 11:
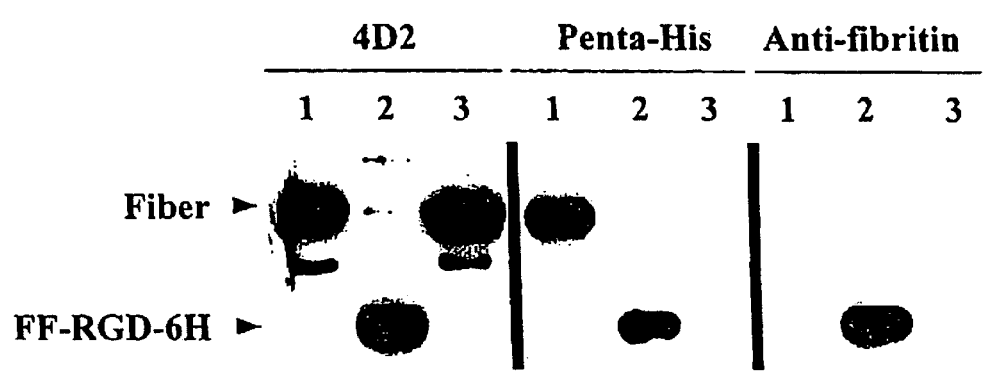
FIG. 11 shows Western blot analysis of FF.RGD/6H chimeras incorporated into Ad5LucFF/6H virions. Proteins of denatured Ad5LucFF.RGD/6H virions, lane 2, were separated on a 10% SDS-PAGE gel and then probed with anti-Ad fiber tail mAb 4D2, anti-5His (SEQ ID NO: 19) mAb Penta-His and anti-fibritin mouse polyclonal antibodies. Wild type Ad5, lane 3, and Ad5LucFc6H, a virus containing fibers with carboxy terminal 6His tags (SEQ ID NO: 17), lane 1, were used as controls.

FF.RGD/6H chimeras present in the preparation of Ad5luc.FF.RGD/6H were further identified by Western blot analysis utilizing a set of antibodies specific to each of the component of the chimeric protein. The presence of the fiber tail domain, the fibritin fragment and the 6His tag (SEQ ID NO: 17) was confirmed by using relevant mono- and polyclonal antibodies (FIG. 11).

Figure 12:
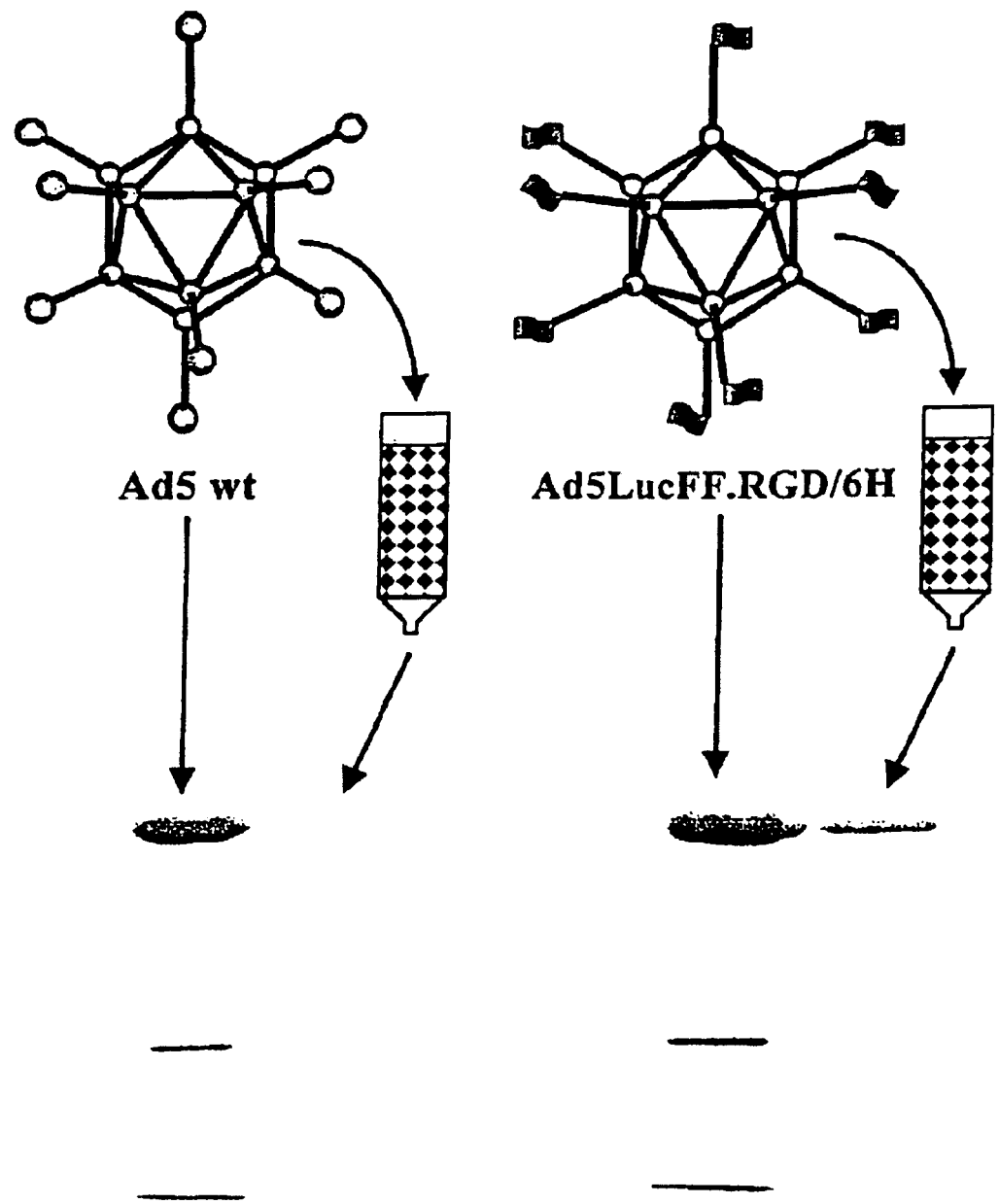
FIG. 12 shows the binding of Ad5LucFF.RGD/6H virions to Ni-NTA-agarose. Wild type Ad5 or Ad5LucFF.RGD/6H were incubated with an aliquot of Ni-NTA-resin. Aliquots of material subsequently eluted from the resin, as well as an aliquot of the virus prior to incubation with Ni-NTA-agarose, were separated on a 10% SDS-PAGE gel and then stained.

Association of the FF.RGD/6H chimeras with the Ad5luc.FF.RGD/6H particles was proved by incubating purified Ad5luc.FF.RGD/6H virions with Ni-NTA-sepharose which is designed for purification of the 6His-tagged (SEQ ID NO: 17) proteins. In contrast to control adenoviral vector containing wild type fibers which did not bind to Ni-NTA, Ad5luc.FF.RGD/6H was efficiently retained on the column. The presence of all major adenoviral capsid proteins in the material eluted from the resin with imidazole suggested that the Ad5luc.FF.RGD/6H virions were anchored to Ni-NTA-sepharose by virtue of the 6His-containing (SEQ ID NO: 17) fiber-fibritin chimeras associated with the virions (FIG. 12).

Figure 13:
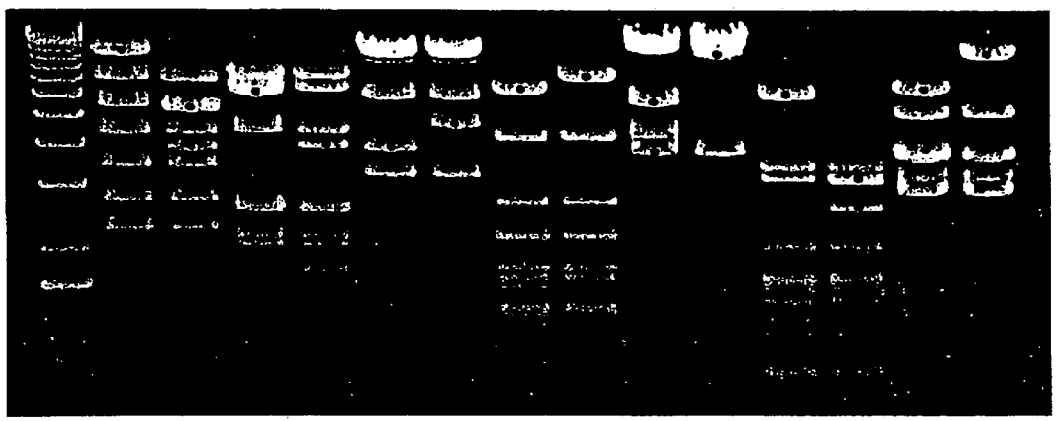
FIG. 13 shows restriction enzyme analysis of Ad5LucFF.RGD/6H. DNA isolated from purified Ad5LucFF.RGD/6H virions was subjected to restriction enzyme analysis using a number of restriction endonucleases. Odd-numbered lanes—control Ad5Luc 1 DNA; even-numbered lanes—Ad5LucFF.RGD/6H DNA.

In order to rule out the possibility of contamination of Ad5luc.FF.RGD/6H preparation with another adenoviral vector, Ad5luc.FF.RGD/6H DNA isolated from virions was subjected to three different assay including restriction enzyme analysis (FIG. 13), "diagnostic" PCR, and sequencing of the fiber-fibritin gene as well as the regions of Ad genome adjacent to it. All three assays showed that the preparation of Ad5luc.FF.RGD/6H is free from any contaminating adenovirus and therefore is suitable for subsequent studies aimed to characterize the gene transfer capacity and the cell entry pathway utilized by Ad5luc.FF.RGD/6H.

To evaluate the gene transfer capacity of Ad5luc.FF.RGD/6H, the virus was employed for gene delivery experiments utilizing two different cell lines: 293 and 293/6H. The latter of the two lines is the derivative of 293 cells constitutively expressing artificial receptor capable of binding 6His-tagged (SEQ ID NO: 17) proteins. The luciferase-expressing adenoviral vector isogenic to Ad5luc.FF.RGD/6H but incorporating the wild type fibers was used in these experiments as a control. The gene transfer with the control virus was done at one multiplicity of infection (MOI), whereas Ad5luc.FF.RGD/6H was used at different MOIs.

Figure 14:
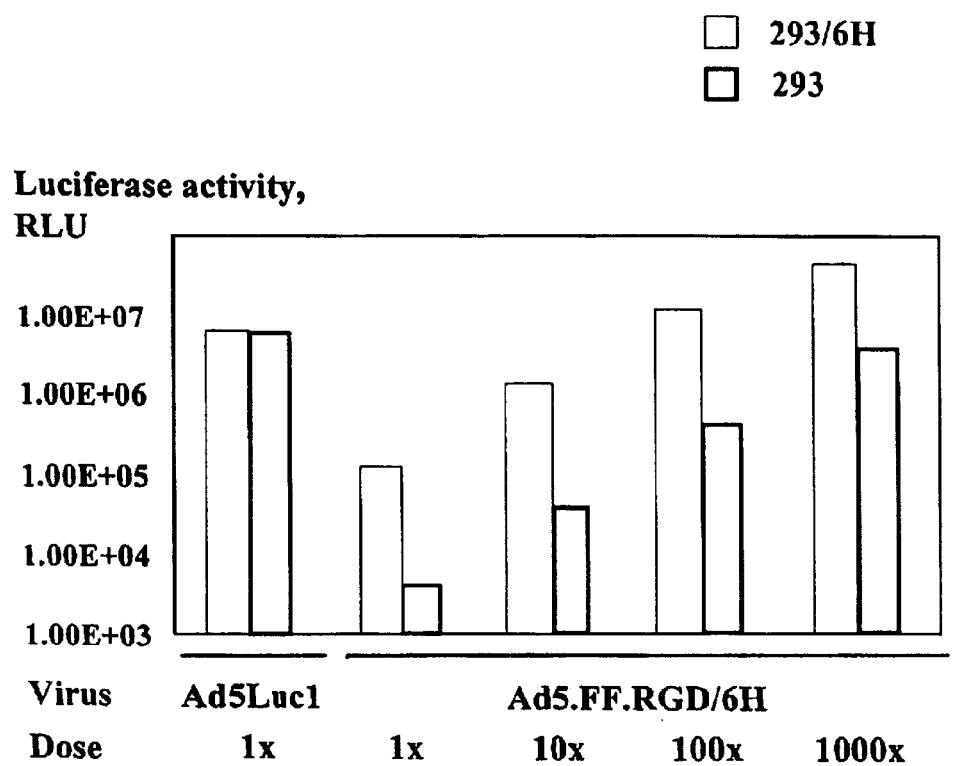
FIG. 14 shows gene transfer by Ad5LucFF.RGD/6H. Cells seeded in 24-well plates were infected with various doses of Ad5LucFF.RGD/6H. The minimal viral dose corresponding to a multiplicity of infection of 40 viral particles per cell, (1×), was equal to the dose of the control virus, Ad5Luc1, whereas Ad5LucFF.RGD/6H doses 10×, 100×, and 1000×contained 10-, 100-, and 1000-times the amount of the control virus, correspondingly. Twenty hours post-infection, the cells were collected, lysed, and the luciferase activity of the lysates was measured in relative light units.

As shown in FIG. 14, Ad5luc.FF.RGD/6H can deliver a luciferase reporter to both types of cells, although with rather different efficiencies (luciferase expression in naive 293 cells was always lower than in 293/6H cells), thereby suggesting that both the RGD-4C (SEQ ID NO: 14 and the 6His peptides (SEQ. ID NO: 17) incorporated within the FF.RGD/6H chimeras functioned as targeting ligands.

The following references were cited herein:

1. Bergelson et al., Science 275, 1320–3 (1997).
2. Tomko et al., Proc. Natl. Acad. Sci. 94, 3352–6 (1997).
3. Krasnykh et al., Molecular Therapy 1, 391–405 (2000).
4. Wickham et al., Nat Biotechnol 14, 1570–3 (1996).
5. Wickham et al., Journal of Virology 71, 8221–8229 (1997).
6. Dmitriev et al., J Virol 72, 9706–13 (1998).
7. Vanderkwaak et al., Gynecol Oncol 74, 227–34 (1999).
8. Kasono et al., Clinical cancer research 5, 2571–2579 (1999).
9. Hong and Engler, J Virol 70, 7071–8 (1996).
10. Tao et al., Structure 5, 789–98 (1997).
11. Letarov et al., Biochemistry (Mosc) 64, 817–23 (1999).
12. V. V. Mesyanzhinov, personal communication.
13. Douglas et al., Nat Biotechnol 17, 470–5 (1999).
14. Krasnykh et al., J Virol 72, 1844–52 (1998).
15. Von Seggern et al., J Gen Virol 79, 1461–8 (1998).
16. Legrand et al., J Virol 73, 907–19 (1999).
17. Davison et al., J Virol 73, 4513–4517 (1999).
18. Lindner et al., Biotechniques 22, 140–9 (1997).
19. Miroshnikov et al., Protein Eng 11, 329–32 (1998).
20. Efimov et al., Virus Genes 10, 173–7 (1995).
21. H. Gahery-Segard, et al., J Virol 72, 2388–97 (1998).
22. Krasnykh et al., J. Virol. 70:6839–46 (1996).

Any patents or publications mentioned in this specification are indicative of the levels of those skilled in the art to which the invention pertains. These patents anD publications are herein incorporate by reference to the same extent as if each individual publication was specifically anD individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, an specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An adenovirus (Ad) with novel vector tropism and ablation of native Ad receptor tropism due to the expression of a fiber replacement protein, said fiber replacement protein comprises:
   a) an amino-terminal portion comprising an adenoviral fiber tail domain that associates with the penton base of the adenovirus;
   b) the fibritin rod trimeric protein that provides trimerization function; and
   c) a carboxy-terminal portion comprising a targeting ligand.

2. The adenovirus of claim 1 wherein the fibritin rod trimeric protein is a fibritin-6His chimera.

3. The adenovirus of claim 1 wherein the fiber-fibritin chimeric rod trimeric protein is a fiber-fibritin-6His chimera.

4. The adenovirus of claim 1, wherein said fiber replacement protein retains trimerism when a sequence encoding a targeting ligand is incorporated into the carboxy-terminus.

5. The adenovirus of claim 1, wherein said fiber replacement protein is soluble.

6. An adenovirus (Ad) with novel vector tropism and ablation of native Ad receptor tropism due to the expression of a fiber replacement protein, said fiber replacement protein comprises:
   a) an amino-terminal portion comprising an adenoviral fiber tail domain that associates with the penton base of the adenovirus;
   b) an isoleucine trimerization motif that provides trimerization function; and
   c) a carboxy-terminal portion comprising a targeting ligand.

7. An adenovirus (Ad) with novel vector tropism and ablation of native Ad receptor tropism due to the expression of a fiber replacement protein, said fiber replacement protein comprises:
   a) an amino-terminal portion comprising an adenoviral fiber tail domain that associates with the penton base of the adenovirus;
   b) a neck region peptide from human lung surfactant D that provides trimerization function; and
   c) a carboxy-terminal portion comprising a targeting ligand.

8. The adenovirus of claim 1, wherein said targeting ligand is selected from the group consisting of physiological ligands, anti-receptor antibodies, cell-specific peptides and single chain antibodies.

9. The adenovirus of claim 1, wherein said adenovirus comprises a transgene.

10. The adenovirus of claim 9, wherein the transgene is a herpes simplex virus thymidine kinase gene.

11. The adenovirus of claim 6, wherein said targeting ligand is selected from the group consisting of physiological ligands, anti-receptor antibodies, cell-specific peptides and single chain antibodies.

12. The adenovirus of claim 6, wherein said adenovirus comprises a transgene.

13. The adenovirus of claim 12, wherein the transgene is a herpes simplex virus thymidine kinase gene.

14. The adenovirus of claim 7, wherein said targeting ligand is selected from the group consisting of physiological ligands, anti-receptor antibodies, cell-specific peptides and single chain antibodies.

15. The adenovirus of claim 7, wherein said adenovirus comprises a transgene.

16. The adenovirus of claim 15, wherein the transgene is a herpes simplex virus thymidine kinase gene.

\* \* \* \* \*

SEQUENCE LISTING

<160> NUMBER OF SEQ ID NOS: 20

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 1
gggaacttga cctcacagaa cgtttatagt cgtttaaatg                              40

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 2
aggccatggc caatttttgc cggcgataaa aaggtag                                 37

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttggccccat ttaaatgaat cgtttgtgtt atgtttcaac gtgtttatt ttc                53

<210> SEQ ID NO 4
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aattgaaaaa taaacacgtt gaaacataac acaaacgatt catttaaatg gggccaatat        60
t                                                                        61

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggcaggtgga ggcggttcag gcggaggtgg ctctggcggt ggcggatccg gggattt          57

<210> SEQ ID NO 6
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
aaatccccgg atccgccacc gccagagcca cctccgcctg aaccgcctcc acctgcc        57

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatctagagg atcgcatcac catcaccatc actaat                               36

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
attagtgatg gtgatggtga tgcgatcctc ta                                   32

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 9
ccctcatgaa gcgcgcaaga ccgtctg                                         27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 10
cccaagctta gtgatggtga tggtgat                                         27

<210> SEQ ID NO 11
<211> LENGTH: 8
<212> TYPE: PRT
<213> ORGANISM: Adenovirus type 5

<400> SEQUENCE: 11

Gly Asn Thr Leu Ser Gln Asn Val
  1               5

<210> SEQ ID NO 12
<211> LENGTH: 26
<212> TYPE: PRT
<213> ORGANISM: Bacteriophage T4

<400> SEQUENCE: 12

Val Tyr Ser Arg Leu Asn Glu Ile Asp Thr Lys Gln Thr Thr Val Glu
  1               5                  10                  15

Ser Asp Ile Ser Ala Ile Lys Thr Ser Ile
             20                  25
```

```
<210> SEQ ID NO 13
<211> LENGTH: 361
<212> TYPE: PRT
<213> ORGANISM: Artificial Sequence
<220> FEATURE:
<223> OTHER INFORMATION: Description of Artificial Sequence: Synthetic
      fiber-fibritin-6H chimera

<400> SEQUENCE: 13
```

| Met | Lys | Arg | Ala | Arg | Pro | Ser | Glu | Asp | Thr | Phe | Asn | Pro | Val | Tyr | Pro |
|---|---|---|---|---|---|---|---|---|---|---|---|---|---|---|---|
| 1 | | | | 5 | | | | | 10 | | | | | 15 | |

| Tyr | Asp | Thr | Glu | Thr | Gly | Pro | Pro | Thr | Val | Pro | Phe | Leu | Thr | Pro | Pro |
|---|---|---|---|---|---|---|---|---|---|---|---|---|---|---|---|
| | | | 20 | | | | | 25 | | | | | 30 | | |

| Phe | Val | Ser | Pro | Asn | Gly | Phe | Gln | Glu | Ser | Pro | Pro | Gly | Val | Leu | Ser |
|---|---|---|---|---|---|---|---|---|---|---|---|---|---|---|---|
| | | 35 | | | | | 40 | | | | | 45 | | | |

| Leu | Arg | Leu | Ser | Glu | Pro | Leu | Val | Thr | Ser | Asn | Gly | Met | Ala | Leu | Lys |
|---|---|---|---|---|---|---|---|---|---|---|---|---|---|---|---|
| | 50 | | | | | 55 | | | | | 60 | | | | |

| Met | Gly | Asn | Gly | Leu | Ser | Leu | Asp | Glu | Ala | Gly | Asn | Leu | Thr | Ser | Gln |
|---|---|---|---|---|---|---|---|---|---|---|---|---|---|---|---|
| 65 | | | | | 70 | | | | | 75 | | | | | 80 |

| Asn | Val | Tyr | Ser | Arg | Leu | Asn | Glu | Ile | Asp | Thr | Lys | Gln | Thr | Thr | Val |
|---|---|---|---|---|---|---|---|---|---|---|---|---|---|---|---|
| | | | | 85 | | | | | 90 | | | | | 95 | |

| Glu | Ser | Asp | Ile | Ser | Ala | Ile | Lys | Thr | Ser | Ile | Gly | Tyr | Pro | Gly | Asn |
|---|---|---|---|---|---|---|---|---|---|---|---|---|---|---|---|
| | | | 100 | | | | | 105 | | | | | 110 | | |

| Asn | Ser | Ile | Ile | Thr | Ser | Val | Asn | Thr | Asn | Thr | Asp | Asn | Ile | Ala | Ser |
|---|---|---|---|---|---|---|---|---|---|---|---|---|---|---|---|
| | | 115 | | | | | 120 | | | | | 125 | | | |

| Ile | Asn | Leu | Glu | Leu | Asn | Gln | Ser | Gly | Gly | Ile | Lys | Gln | Arg | Leu | Thr |
|---|---|---|---|---|---|---|---|---|---|---|---|---|---|---|---|
| | 130 | | | | | 135 | | | | | 140 | | | | |

| Val | Ile | Glu | Thr | Ser | Ile | Gly | Ser | Asp | Asp | Ile | Pro | Ser | Ser | Ile | Lys |
|---|---|---|---|---|---|---|---|---|---|---|---|---|---|---|---|
| 145 | | | | | 150 | | | | | 155 | | | | | 160 |

| Gly | Gln | Ile | Lys | Asp | Asn | Thr | Thr | Ser | Ile | Glu | Ser | Leu | Asn | Gly | Ile |
|---|---|---|---|---|---|---|---|---|---|---|---|---|---|---|---|
| | | | | 165 | | | | | 170 | | | | | 175 | |

| Val | Gly | Glu | Asn | Thr | Ser | Ser | Gly | Leu | Arg | Ala | Asn | Val | Ser | Trp | Leu |
|---|---|---|---|---|---|---|---|---|---|---|---|---|---|---|---|
| | | | 180 | | | | | 185 | | | | | 190 | | |

| Asn | Gln | Ile | Val | Gly | Thr | Asp | Ser | Ser | Gly | Gln | Pro | Ser | Pro | Pro |
|---|---|---|---|---|---|---|---|---|---|---|---|---|---|---|
| | 195 | | | | | 200 | | | | | 205 | | | |

| Gly | Ser | Leu | Leu | Asn | Arg | Val | Ser | Thr | Ile | Glu | Thr | Ser | Val | Ser | Gly |
|---|---|---|---|---|---|---|---|---|---|---|---|---|---|---|---|
| | 210 | | | | | 215 | | | | | 220 | | | | |

| Leu | Asn | Asn | Asp | Val | Gln | Asn | Leu | Gln | Val | Glu | Ile | Gly | Asn | Asn | Ser |
|---|---|---|---|---|---|---|---|---|---|---|---|---|---|---|---|
| 225 | | | | | 230 | | | | | 235 | | | | | 240 |

| Thr | Gly | Ile | Lys | Gly | Gln | Val | Val | Ala | Leu | Asn | Thr | Leu | Val | Asn | Gly |
|---|---|---|---|---|---|---|---|---|---|---|---|---|---|---|---|
| | | | | 245 | | | | | 250 | | | | | 255 | |

| Thr | Asn | Pro | Asn | Gly | Ser | Thr | Val | Glu | Glu | Arg | Gly | Leu | Thr | Asn | Ser |
|---|---|---|---|---|---|---|---|---|---|---|---|---|---|---|---|
| | | | 260 | | | | | 265 | | | | | 270 | | |

| Ile | Lys | Ala | Asn | Glu | Thr | Asn | Ile | Ala | Ser | Val | Thr | Gln | Glu | Val | Asn |
|---|---|---|---|---|---|---|---|---|---|---|---|---|---|---|---|
| | | 275 | | | | | 280 | | | | | 285 | | | |

| Thr | Ala | Lys | Gly | Asn | Ile | Ser | Ser | Leu | Gln | Gly | Asp | Val | Gln | Ala | Leu |
|---|---|---|---|---|---|---|---|---|---|---|---|---|---|---|---|
| | 290 | | | | | 295 | | | | | 300 | | | | |

| Gln | Glu | Ala | Gly | Tyr | Ile | Pro | Glu | Ala | Pro | Arg | Asp | Gly | Gln | Ala | Tyr |
|---|---|---|---|---|---|---|---|---|---|---|---|---|---|---|---|
| 305 | | | | | 310 | | | | | 315 | | | | | 320 |

| Val | Arg | Lys | Asp | Gly | Glu | Trp | Val | Leu | Leu | Ser | Thr | Phe | Leu | Ser | Pro |
|---|---|---|---|---|---|---|---|---|---|---|---|---|---|---|---|
| | | | 325 | | | | | 330 | | | | | 335 | | |

| Ala | Gly | Gly | Gly | Gly | Ser | Gly | Gly | Gly | Ser | Gly | Gly | Gly | Gly | Ser |
|---|---|---|---|---|---|---|---|---|---|---|---|---|---|---|
| | | | 340 | | | | | 345 | | | | | 350 | |

| Arg | Gly | Ser | His | His | His | His | His | His |
|---|---|---|---|---|---|---|---|---|
| | | 355 | | | | | 360 | |

```
<210> SEQ ID NO 14
<211> LENGTH: 9
<212> TYPE: PRT
<213> ORGANISM: Unknown Organism
<220> FEATURE:
<223> OTHER INFORMATION: Description of Unknown Organism: Peptide ligand
      containing the RGD motif

<400> SEQUENCE: 14

Cys Asp Cys Arg Gly Asp Cys Phe Cys
  1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide fragment from FF/6H chimera

<400> SEQUENCE: 15

Phe Asn Pro Val Tyr Asp
  1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide fragment from FF/6H chimera

<400> SEQUENCE: 16

Arg Gly Ser His His His His His His
  1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 17

His His His His His His
  1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide fragment from FF/6H chimera

<400> SEQUENCE: 18

Ser Gln Asn Val
  1

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: 5-His tag
```

```
<400> SEQUENCE: 19

His His His His His
  1               5

<210> SEQ ID NO 20
<211> LENGTH: 4
<212> TYPE: PRT
<213> ORGANISM: Bacteriophage T4

<400> SEQUENCE: 20

Gly Leu Asn Thr
  1
```